United States Patent [19]

De Lay

[11] 4,259,320

[45] Mar. 31, 1981

[54] CONCURRENT USE OF AVOPARCIN WITH GROWTH-PROMOTING IMPLANTS IN CATTLE

[75] Inventor: Roger L. De Lay, Hamilton Square, N.J.

[73] Assignee: American Cyanamid Company, Stamford, Conn.

[21] Appl. No.: 17,004

[22] Filed: Mar. 2, 1979

[51] Int. Cl.³ .............................................. A61K 35/00
[52] U.S. Cl. ................................................... 424/118
[58] Field of Search ...................... 424/118, 124, 238

[56] References Cited

U.S. PATENT DOCUMENTS

| | | | |
|---|---|---|---|
| 2,895,875 | 7/1959 | Klette | 424/238 |
| 3,338,786 | 8/1967 | Kunstmann | 424/118 |
| 3,832,462 | 8/1974 | Shu et al. | 424/123 |
| 3,855,410 | 12/1974 | Dann et al. | 424/124 |
| 3,856,937 | 12/1974 | Waite | 424/115 |
| 3,954,973 | 5/1976 | Hlavka et al. | 424/118 |
| 4,124,626 | 11/1978 | Wood | 424/118 |

FOREIGN PATENT DOCUMENTS 2752566 1/1978 Fed. Rep. of Germany .......... 424/124

*Primary Examiner*—Frederick E. Waddell
*Attorney, Agent, or Firm*—H. G. Jackson

[57] ABSTRACT

This disclosure describes a combination treatment for ruminants to synergistically enhance the growth rate thereof and improve the efficiency of feed utilization thereby. The treatment involves, orally administering a growth-enhancing amount of the antibiotic AV290, antibiotic AV290 sulfate, antibiotic AV290-syntan complex, antibiotic AV290-alkyl sulfate complex and/or antibiotic AV290 alkylated derivative, to ruminants which have been parenterally or orally treated with a growth-enhancing amount of a selected steroid or steroidal composition.

7 Claims, No Drawings

CONCURRENT USE OF AVOPARCIN WITH GROWTH-PROMOTING IMPLANTS IN CATTLE

SUMMARY OF THE INVENTION

This invention relates to a novel method for treating ruminants to synergistically enhance the growth rate thereof and improve the efficiency of feed utilization thereby; comprising, parenterally or orally administering to said ruminants, preferably in the form of a medicated implant, a growth-promoting amount of a composition or compound selected from the group consisting of (1) progesterone plus estradiol benzoate; (2) testosterone plus estradiol benzoate; (3) diethylstilbestrol; and (4) 3,4,5,6,7,8,9,10,11,12-decahydro-7,14,16-trihydroxy-3-methyl-1$\underline{H}$-2-benzoxacyclotetradecin-1-one; and orally administering, in or with the feed of said parenterally treated ruminants, a growth-enhancing amount of one or more of the following active ingredients:

(1) antibiotic AV290, whose preparation and properties are disclosed in U.S. Pat. No. 3,338,786;

(2) antibiotic AV290 sulfate, which is disclosed in U.S. Pat. No. 3,855,410;

(3) an antibiotic AV290-syntan complex, prepared as described in U.S. Pat. No. 3,832,462;

(4) an antibiotic AV290-alkyl sulfate complex, derived by treatment of the antibiotic with an alkali metal alkyl sulfate as set forth in U.S. Pat. No. 3,856,937;

(5) an antibiotic AV290 alkylated derivtive, derived by treatment of the antibiotic with a lower alkyl halide as defined and described in U.S. Pat. No. 3,954,973.

My invention is based upon the discovery that, although the above-described steroidal compositions and AV290 antibiotics have been separately utilized for promoting the growth rate of poultry and farm animals, heretofore-said AV290 antibiotics have not been used in conjunction with the above-identified growth-promoting steroids for the treatment of ruminants.

It was, therefore, surprising to find that the growth rate of ruminants, particularly cattle, could be synergistically enhanced using a combination treatment involving oral administration of antibiotic AV290 or a pharmaceutically acceptable salt, complex or alkylated derivative thereof, and concurrent parenteral treatment of said ruminants with one of the above-identified steroids or steroidal compositions.

The above-cited U.S. Pat. Nos. 3,338,786; 3,832,462; 3,855,410; 3,856,937; and 3,954,973, are hereby incorporated by reference.

Increasing consumption of meat products by the world's expanding population has prompted the animal science industry, in recent years, to make a concerted effort to find new and more effective means for enhancing the growth rate of meat-producing animals and increasing the efficiency of feed utilization by such animals. To this end, they have evaluated a myriad of chemical compositions and have met with some limited success in this area of investigation. However, it is exceedingly obvious to the skilled investigator that world needs demand still further improvement in methods for enhancing the growth rate of meat-producing animals and improving the efficiency of the utilization of animal feed thereby, if the world's feed requirements are to be met or even improved.

It is, therefore, an object of this invention to provide a method for treating ruminant animals, particularly cattle, for enhancing the growth rate thereof and improving the efficiency of feed utilization thereby.

In accordance with this invention, it has been found that the growth rate of beef cattle, weighing about 180 kg to 500 kg, can be synergistically enhanced and their utilization of feed improved by parenterally administering to said cattle a growth-enhancing amount of a steroid or steroidal composition selected from the group consisting of:

(a) 150–250 mg progestrone plus 10–30 mg estradiol benzoate;

(b) 150–250 mg testosterone plus 10–30 mg estradiol benzoate;

(c) 25–50 mg 3,4,5,6,7,8,9,10,11,12-decahydro-7,14,16-trihydroxy-3-methyl-1$\underline{H}$-2-benzoxacyclotetradecin-1-one; or (d) 12–36 mg diethylstilbestrol;

and, orally administering to said animals, a feed containing from about 30 ppm to 100 ppm (100% dry matter basis), and preferably 40 ppm and 75 ppm (100% dry matter basis) of antibiotic AV290, antibiotic AV290 sulfate, antibiotic AV290-syntan complex, antibiotic AV290-alkyl sulfate complex or antibiotic AV290 alkylated derivative.

Since cattle generally consume, each day, an amount of feed dry matter approximately equivalent to about 2.5% of their body weight, cattle weighing between about 180 kg and 500 kg, offered feed containing 30 ppm to 100 ppm of the antibiotic, consume between about 150 mg and 1250 mg/head/day of said antibiotic. When feeds containing the preferred 40 ppm to 75 ppm of AV290 antibiotic are offered, each animal consumes the preferred regimen of about 200 mg to 1000 mg/head/day of said antibiotic.

Preferred levels of steroid or steroidal composition are as follows:

(a) 200 mg progestrone plus 20 mg estradiol benzoate;

(b) 200 mg testosterone plus 20 mg estradiol benzoate;

(c) 36 mg 3,4,5,6,7,8,9,10,11,12-decahydro-7,14,16-trihydroxy-3-methyl-1$\underline{H}$-2-benzoxacyclotetradecin-1-one; or (d) 12–36 mg diethylstilbestrol.

In practice, it has been found most effective to administer the steroid or steroidal composition as a subcutaneous injection of pellets under the skin of the ears of the animals.

With drugs such as progestrone plus estradiol benzoate; testosterone plus estradiol benzoate or diethylstilbestrol, approximately 85% to 95% by weight of the active ingredient is mixed with about 5% to 15% of an inert diluent such as corn starch or acacia. A lubricant, such as magnesium stearate, may also be used, if so desired, to aid in the manufacture of the pellets.

Pellets containing an effective level of 3,4,5,6,7,8,9,10,11,12-decahydro-7,14,16-trihydroxy-3-methyl-1$\underline{H}$-2-benzoxacyclotetradecin-1-one can be prepared by admixing the above-said active ingredient with a diluent such as carbowax, carnuba wax, or the like. A lubricant, such as magnesium or calcium stearate, may be added to improve the pelleting process. Where desired, the above-named benzoxacyclotetradecin-1-one may be prepared as a paste dispersed in peanut oil and administered as a paste implant under the skin of the ear of the animal in which enhanced growth promotion is sought.

Advantageously, it has been found that in practicing the method of the present invention, a second implant, administered about 16 weeks after the first implantation, will further synergize the growth rate of cattle receiving the antibiotic AV290 or the pharmaceutically acceptable salt, complex or alkylated derivative thereof, with their daily ration.

Animal feeds containing the desired level of AV290 antibiotic are generally prepared by admixing the selected feed with the dried AV290 antibiotic or the pharmaceutical salt, complex or alkylated derivative thereof, or the dried harvest mash solids from the antibiotic fermentation process, either alone or in combination with suitable carriers.

The milligrams per kilogram of antibiotic present in any particular supplement composition utilized in the present invention may be readily determined by bioassay (after adjusting the pH to 8.0-9.0) as set forth in U.S. Pat. No. 3,338,786. The preferred method is an adaptation of the *Staphylococcus aureus* turbidimeteric assay for tetracycline that is described in the manual, "Assay Methods of Antibiotics, A Laboratory Manual," by D. C. Groves and W. A. Randall, Medical Encyclopedia Inc. (1955), pages 48-52. From the potency data thus-obtained, the amount of feed supplement composition to be used per ton of feed may be readily calculated.

A wide variety of carrier may be used in the preparation of the feed supplement compositions used in the present invention. Carriers suitable for use to make up the feed supplement compositions include the following: soybean meal, alfalfa meal, cottonseed oil meal, linseed oil meal, sodium chloride, cornmeal, cane molasses, urea, bone meal, corncob meal, and the like. The carrier promotes a uniform distribution of the antibiotic, the antibiotic salt, the antibiotic complex, or the alkylated derivative of said antibiotic, in the finished feed into which the supplement is blended. It thus performs an important function by ensuring proper distribution of the antibiotic throughout the feed.

If the supplement is used as a top dressing for feed, it, likewise, helps to ensure uniformity of distribution of said antibiotic across the top dressed feed.

The invention is further demonstrated by the example set forth below.

EXAMPLE 1

Ninety-six cattle, with an initial average weight of 340 kg, were divided into 24 pens for four head each. Four pens received only the basal ration (controls); four pens received antibiotic AV290 sodium lauryl sulfate incorporated into the basal ration at a level of 50 ppm, determined on the basis of dry matter in said ration; eight pens received and basal ration and were implanted with 200 mg progestrone plus 20 mg estradiol benzoate; eight pens received both the implants (200 mg progestrone plus 20 mg estradiol benzoate) and the antibiotic AV290 sodium lauryl sulfate (50 ppm), determined on the basis of dry matter in the basal ration. Feed and water were administered ad libitum throughout the test period.

The ration, offered free choice to the cattle calculated on a 100% dry matter basis, consisted of the following feedstuffs:

| Composition | % by Weight |
|---|---|
| High Moisture Shelled Corn | 55 |
| Hay Crop Silage | 40 |

| Composition | % by Weight |
|---|---|
| AV290 Sodium Lauryl Sulfate Treated or Untreated Premix | 5 |

The premix for those pens of cattle receiving AV290 sodium lauryl sulfate consisted of:

| Composition | % by Weight |
|---|---|
| Trace Mineralized Salt (Iodized Cobalt Salt) | 7 |
| Dicalcium Phosphate | 10 |
| 7% Av290 Sodium Lauryl Sulfate Premix (83.3% dried *Streptomyces candidis*) | 1.428 |
| Ground Corn | 81.572 |

The premix for those pens of cattle not receiving AV290 sodium lauryl sulfate consisted of:

| Composition | % by Weight |
|---|---|
| Trace Mineralized Salt (Iodized Cobalt Salt) | 7 |
| Dicalcium Phosphate | 10 |
| Ground Corn | 83 |

All cattle were weighed before the start of the test and their weights recorded. Implants were inserted subcutaneously under the skin in the ears of cattle, in pens selected for evaluation of the growth enhancement effects of implants alone and those cattle selected for evaluation of the growth enhancement effects of implants used in conjunction with an AV290 sodium lauryl sulfate medicated feed.

Records of feed consumption were maintained throughout the experiment, and the cattle weighed periodically to determine their weight gain. At 112 days into the experiment, all cattle were weighed, and their average daily gain determined. Average daily feed consumed and feed per kg of gain were also determined. These data are reported in Table I below.

After the cattle were weighed and feed consumption determined for all pens of animals, half of the pens of cattle that had received either implants alone or implants plus the AV 290 sodium lauryl sulfate medicated feed during the first 112 days of the experiment, were given a second implant. The implant was administered as before, subcutaneously under the skin of the ear of the cattle. The cattle were returned to their pens, weighed periodically, and the feed consumption for each pen recorded.

After 182 days, the cattle were again weighed and their feed consumption determined. Data obtained are reported in Table II, where it can be seen that both the growth rate and the efficiency of feed utilization were synergistically enhanced in cattle receiving both the implants at the start of the experiment and the AV290 sodium lauryl sulfate medicated feed throughout the experiment. Surprisingly, it was also found that the cattle receiving implants at the start of the test and again at 112 days into the test plus AV290 sodium lauryl sulfate throughout the entire 182-day experiment, exhibited a further synergistic enhancement in both their growth rate and their efficiency of feed utilization.

TABLE I

Evaluation of 50 ppm of AV290 Sodium Lauryl Sulfate Medicated Feed Alone or in Conjunction with 200 mg Progesterone plus 20 mg Estradiol Benzoate, Administered as an Implant, on the Growth Rate and Efficiency of Feed Utilization by Cattle Over a 112-Day Evaluation Period.

| Treatment | Average Daily Gain (kg) | % Improvement Over Controls | Average Daily Feed* (kg) | Feed/Gain | % Improvement Over Controls |
|---|---|---|---|---|---|
| Control | 1.03 | — | 15.51 | 15.06 | — |
| 50 ppm AV290 Sodium Lauryl Sulfate | 1.17 | 13.6 | 14.90 | 12.74 | 15.4 |
| Implant (200 mg Progesterone plus 20 mg Estradiol Benzoate) | 1.11 | 7.8 | 15.59 | 14.05 | 6.7 |
| 50 ppm AV290 Sodium Lauryl Sulfate plus (200 mg Progesterone plus 20 mg Estradiol Benzoate Implant) | 1.33 | 29.1 | 15.19 | 11.42 | 24.2 |

*Feed contained 45% dry matter.

TABLE II

Evaluation of 50 ppm of AV290 Sodium Lauryl Sulfate Medicated Feed Alone or in Conjunction with 200 mg Progesterone plus 20 mg Estradiol Benzoate Administered Once as a Subcutaneous Implant at the Start of the Test, or Once at the Start and Again After 112 Days; on the Growth Rate and Efficiency of Feed Utilization by Cattle Over a 182-Day Evaluation Period.

| Treatment | Average Daily Gain (kg) | | Average Daily Feed** (kg) | Feed/Gain | |
|---|---|---|---|---|---|
| Control | 0.94 | (—) | 15.56 | 16.61 | (—) |
| 50 ppm AV290 Sodium Lauryl Sulfate Medicated Feed | 1.00 | (6.4)* | 14.82 | 14.84 | (10.6)* |
| 200 mg Progesterone plus 20 mg Estradiol Benzoate - Single Implant (Day 0) | 1.02 | (8.5)* | 15.70 | 15.48 | (6.8)* |
| 200 mg Progesterone plus 20 mg Estradiol Benzoate - Single Implant (Day 0) plus 50 ppm AV290 Sodium Lauryl Sulfate Medicated Feed | 1.17 | (24.5)* | 15.30 | 13.13 | (21.0)* |
| 2 Implants (Day 0 and Day 112) 200 mg Progesterone plus 20 mg Estradiol Benzoate | 1.11 | (18.1)* | 16.37 | 14.79 | (11.0)* |
| 2 Implants (Day 0 and Day 112) 200 mg Progesterone plus 20 mg Estradiol Benzoate plus 50 ppm AV290 Sodium Lauryl Sulfate Medicated Feed | 1.28 | (36.2)* | 15.80 | 12.48 | (24.9)* |

*Percent improvement over control.
**Feed contained 45% dry matter.

I claim:

1. A method for synergistically enhancing the growth rate and efficiency of feed utilization of ruminants; comprising, parenterally administering to said ruminants weighing between 180 kg and 500 kg a growth-enhancing amount of a compound or composition selected from the group consisting of:
   (1) progesterone plus estradiol benzoate;
   (2) testosterone plus estradiol benzoate; and
   (3) 3,4,5,6,7,8,9,10,11,12-decahydro-7,14,16-trihydroxy-3-methyl-1H-2-benzoxacyclotetradecin-1-one;

and in conjunction therewith, orally administering to said ruminants, in or with their feed, a growth-enhancing amount of antibiotic selected from the group consisting of: AV290, antibiotic AV290 sulfate, antibiotic AV290-syntan complex, antibiotic AV290-alkyl sulfate, or antibiotic AV290 alkylated derivative and mixtures thereof.

2. A method according to claim 1, wherein said orally administered AV290 antibiotic, AV290 sulfate, AV290-syntan complex, AV290 alkyl sulfate, AV290 alkylated derivative or mixtures thereof is administered to said ruminants in a feed containing 30 ppm to 100 ppm of said antibiotic determined on the basis of dry matter in said feed; and said parenterally administered compound or composition is administered as a subcutaneous implant under the skin of the ears of said ruminants and is selected from the group consisting of implants containing:
   (1) 150 mg to 250 mg progesterone plus 10 mg to 30 mg estradiol benzoate;
   (2) 150 mg to 250 mg testosterone plus 10 mg to 30 mg of estradiol benzoate; or,
   (3) 25 mg to 50 mg 3,4,5,6,7,8,9,10,11,12-decahydro-7,14,16-trihydroxy-3-methyl-1H-2-benzoxacyclotetradecin-1-one.

3. A method according to claim 2, wherein said orally administered antibiotic is administered to ruminants at a dose level of from 150 mg to 1250 mg/head/day.

4. A method for synergistically enhancing the growth rate and efficiency of feed utilization of cattle weighing between 180 kg and 500 kg; comprising, orally administering to said cattle a feed containing from 40 ppm to 75 ppm (dry weight basis) of AV290 sodium lauryl sulfate, and in conjunction therewith parenterally administering to said cattle a subcutaneous implant containing 200 mg of progesterone and 20 mg of estradiol benzoate.

5. A method according to claim 4, wherein said cattle feed contains 50 ppm of AV290 sodium lauryl sulfate.

6. A method for synergistically enhancing the growth rate and efficiency of feed utilization of cattle weighing between 180 kg and 500 kg; comprising, orally administering to said cattle, in or with their feed, from 250 mg to 625 mg per head per day of antibiotic AV290 sodium lauryl sulfate; and in conjunction therewith, administering to said cattle a subcutaneous implant containing 200 mg of progesterone and 20 mg of estradiol benzoate.

7. A method for synergistically enhancing the growth rate and efficiency of feed utilization of cattle weighing between 180 kg and 500 kg; comprising, orally administering to said cattle, in or with their feed, about 350 mg per head per day of antibiotic AV290 sodium lauryl sulfate; and in conjunction therewith, administering to said cattle a subcutaneous implant containing 200 mg of progesterone and 20 mg of estradiol benzoate.

* * * * *